(12) United States Patent
Basiri

(10) Patent No.: US 11,445,947 B2
(45) Date of Patent: *Sep. 20, 2022

(54) METHODS AND APPARATUS FOR MEASURING BLOOD OXYGENATION OF TISSUE

(71) Applicant: BIOXYTECH RETINA, INC., Richmond, CA (US)

(72) Inventor: Ali Basiri, Pleasant Hill, CA (US)

(73) Assignee: Bioxytech Retina, Inc., Richmond, CA (US)

( * ) Notice: Subject to any disclaimer, the term of this patent is extended or adjusted under 35 U.S.C. 154(b) by 237 days.

This patent is subject to a terminal disclaimer.

(21) Appl. No.: 16/884,747

(22) Filed: May 27, 2020

(65) Prior Publication Data

US 2021/0100484 A1 Apr. 8, 2021

Related U.S. Application Data

(63) Continuation of application No. 16/004,307, filed on Jun. 8, 2018, now Pat. No. 10,694,985, which is a
(Continued)

(51) Int. Cl.
*G01J 3/04* (2006.01)
*A61B 5/1455* (2006.01)
(Continued)

(52) U.S. Cl.
CPC ............ *A61B 5/1455* (2013.01); *A61B 3/145* (2013.01); *A61B 5/14552* (2013.01);
(Continued)

(58) Field of Classification Search
CPC ... A61B 5/1455; A61B 3/145; A61B 5/14552; A61B 5/7257; A61B 5/14555;
(Continued)

(56) References Cited

U.S. PATENT DOCUMENTS

| 5,822,035 A | 10/1998 | Bille |
| 6,819,949 B2 | 11/2004 | Smith et al. |

(Continued)

FOREIGN PATENT DOCUMENTS

| WO | WO-2014146053 A2 | 9/2014 |
| WO | WO-2014151114 A1 | 9/2014 |

(Continued)

OTHER PUBLICATIONS

PCT/US2016/065990 International Search Report and Written Opinion dated Mar. 15, 2017.

*Primary Examiner* — Md M Rahman
(74) *Attorney, Agent, or Firm* — Wilson Sonsini Goodrich & Rosati

(57) ABSTRACT

An apparatus and method of measuring oxygenation of tissue in a non-invasive manner are provided. The apparatus comprises a light source configured to emit a light pattern to be projected onto the tissue, in which the light pattern comprises superimposed patterns having different patterns. A detector captures an image of a reflected light pattern which is reflected from the tissue as a result of the projected light pattern. A processor coupled to the detector can be configured to perform a transform on the image of the reflected light pattern and determine oxygenation of each of a plurality of layers of the tissue in response to the transform of the image. Polarimetry can be used in determining a change in polarization angle of light beam. Tissue oxygenation can be determined at a plurality of layers from one snapshot, for example oxygenation of retinal layers.

20 Claims, 4 Drawing Sheets

Related U.S. Application Data continuation of application No. PCT/US2016/065990, filed on Dec. 9, 2016.

(60) Provisional application No. 62/265,959, filed on Dec. 10, 2015.

(51) Int. Cl.
*A61B 3/14* (2006.01)
*A61B 5/00* (2006.01)
*G06T 7/00* (2017.01)
*G06V 10/60* (2022.01)

(52) U.S. Cl.
CPC .......... *A61B 5/7257* (2013.01); *G06T 7/0012* (2013.01); *A61B 5/14555* (2013.01); *A61B 2562/0242* (2013.01); *G06T 2207/30041* (2013.01); *G06V 10/60* (2022.01)

(58) Field of Classification Search
CPC .......... A61B 2562/0242; G06T 7/0012; G06T 2207/30041; G06V 10/60
USPC ......................................................... 356/310
See application file for complete search history.

(56) References Cited

U.S. PATENT DOCUMENTS

| | | |
|---|---|---|
| 6,958,815 B2 | 10/2005 | Bevilacqua et al. |
| 7,333,842 B2 | 2/2008 | Schweitzer et al. |
| 7,575,321 B2 | 8/2009 | Newman et al. |
| 8,109,634 B2 | 2/2012 | Gil |
| 8,308,299 B2 | 11/2012 | Ramella-Roman et al. |
| 8,382,284 B2 | 2/2013 | Munger et al. |
| 8,491,120 B2 | 7/2013 | Kahn et al. |
| 8,706,178 B2 | 4/2014 | Denninghoff et al. |
| 8,892,192 B2 | 11/2014 | Cuccia et al. |
| 9,078,602 B2 | 7/2015 | Plaian et al. |
| 9,220,412 B2 | 12/2015 | Cuccia |
| 9,274,047 B2 | 3/2016 | Velten et al. |
| 9,277,866 B2 | 3/2016 | Cuccia |
| 2002/0188203 A1 | 12/2002 | Smith et al. |
| 2005/0288565 A1 | 12/2005 | Kerr |
| 2007/0219439 A1 | 9/2007 | Vilser et al. |
| 2009/0099428 A1 | 4/2009 | Munger et al. |
| 2009/0153798 A1 | 6/2009 | Dick et al. |
| 2010/0030042 A1 | 2/2010 | Denninghoff et al. |
| 2010/0085537 A1 | 4/2010 | Ramella-Roman et al. |
| 2010/0094135 A1 | 4/2010 | Fang-Yen et al. |
| 2010/0238404 A1 | 9/2010 | Newman et al. |
| 2011/0043756 A1 | 2/2011 | Kahn et al. |
| 2012/0093389 A1 | 4/2012 | Halldorsson et al. |
| 2013/0128225 A1 | 5/2013 | Wall et al. |
| 2015/0141839 A1 | 5/2015 | Cuccia et al. |
| 2016/0120404 A1 | 5/2016 | Jordan et al. |
| 2016/0302669 A1 | 10/2016 | Cuccia |

FOREIGN PATENT DOCUMENTS

| | | |
|---|---|---|
| WO | WO-2015105689 A1 | 7/2015 |
| WO | WO-2017100685 A1 | 6/2017 |

METHODS AND APPARATUS FOR MEASURING BLOOD OXYGENATION OF TISSUE

CROSS-REFERENCE

This application is a continuation application of U.S. application Ser. No. 16/004,307, filed Jun. 8, 2018, which is a continuation of PCT International Application No. PCT/US2016/065990, filed on Dec. 9, 2016, which claims priority from U.S. provisional Application No. 62/265,959, filed on Dec. 10, 2015, and to which application we claim priority under 35 USC § 120. Each of the above-referenced applications is hereby incorporated by reference in its entirety.

BACKGROUND OF THE INVENTION

Tissue oxygenation is an important physiological parameter in at least some instances. Abnormal oxygenation of tissues and blood is implicated in a number of diseases preceding tissue damage, including infectious processes, diabetic retinopathy, choroidal disorders, stroke and cancer. For instance, the retinal vasculature's oxygen saturation ($SO_2$) is a valuable indicator of disease, in particular for patients with diabetic retinopathy (DR) who may experience changes in retinal oxygen saturation during their lifetime. A broad range of studies have shown that the earliest detectable sign of DR is an increase of ~4% in the $SO_2$ in the retinal veins. Once DR is detected, there are treatment options available to slow or stop DR progression and prevent retinal structural damage. The Early Treatment Diabetic Retinopathy Study (ETDRS), a multicenter clinical trial funded by the NEI, aims to determine whether the progress of DR could be slowed or stopped using either argon laser photocoagulation or aspirin treatment. Although a number of experimental systems aimed at measuring retinal $SO_2$ have been developed, a reliable, robust model for in vivo monitoring is still lacking.

Prior methods and apparatus of measuring oxygenation of the tissue can be less than ideal. The prior methods and apparatus can be more complex and less accurate than would be ideal, and may not be well suited for tissue oxygenation mapping. For example, tissue can move and degrade measurements and the prior methods and apparatus can be less than ideally suited to measure tissue quickly. Measurements of retinal tissue of the eye can be subject to movement when the eye moves, and ocular measurements of the retina can be more difficult and less accurate than would be ideal.

In light of the above it would be desirable to have improved measurements to measure oxygenation of tissue.

SUMMARY OF THE INVENTION

The methods and apparatus disclosed herein provide improved measurements of tissue oxygenation with decreased measurement times and improved measurement accuracy. The methods and apparatus disclosed herein are capable of measuring oxygenation of the tissue with a reduced number of image frames captured by a detector comprising a plurality of pixels, which substantially prevents a degrading in measurement caused by a movement of the tissue during the measurement and improves the accuracy. In some embodiments, single snapshot of the tissue can be used to determine and map blood oxygenation. The methods and apparatus disclosed herein are particularly advantageous in measuring oxygenation of tissue such as retinal tissue of the eye.

A light pattern having superimposed patterns can be projected onto the tissue, and a reflected light pattern can be imaged by a detector (e.g., a CCD). The light pattern imaged by the detector can be transformed with a transform function to generate a transform data, and the transform data can be used to determine the oxygenation of the tissue. A map of tissue oxygenation can be determined in response to the transform data from a single measurement frame (e.g., a single snapshot of the tissue) from the detector and displayed to a user.

The methods and apparatus disclosed herein can determine oxygenation of the tissue at a plurality of layers. In some instances, the apparatus can comprise an ellipsometer to determine oxygenation of the tissue at each of a plurality of layers of the tissue. The projected light pattern can comprise modulated polarized light. The reflectance and polarization change through different retinal layers can be measured. The information on absorption can be obtained from the change of reflectance for different spatial frequencies. The optical information on different layers can be obtained from the shift of polarization angle. In contrary to a conventional ellipsometry where one would need to scan a range of incidence angles to reconstruct the polarization angle changes, with the methods and apparatus disclosed herein, each spatial frequency corresponds to a unique incidence angle, thus, in one snapshot, all the information needed to map the multilayer retinal structure can be captured.

In the methods and apparatus disclosed herein, modulated light can be used, which provides at least two independent radiations in one snapshot. This empowers ellipsometer to capture reflectance at different angles in one snapshot, and allows to determine the optical properties of different layers up to the choroid.

In the methods and apparatus disclosed herein, oxygenation of the tissue can be calculated in one snapshot by using an image splitter, which also eliminating the need for eye dilation by using near-infrared (NIR) radiation or laser. In some instances, in case light beam of visible wavelengths is used, eye dilation may be required.

An aspect of the disclosure may provide a method of measuring oxygenation of tissue. The method can comprise projecting a light pattern onto the tissue, said light pattern comprising a superimposed patterns having two or more different patterns; imaging a reflected light pattern which is reflected from the tissue as a result of the projected light pattern; performing a transform on the reflected light pattern; and determining oxygenation of each of a plurality of layers of the tissue in response to the transform of the reflected light pattern.

Aspects of the disclosure may also provide an apparatus to measure oxygenation of tissue. The apparatus can comprise: a light source configured to emit a light pattern to be projected onto the tissue, said light pattern comprising a superimposed patterns having two or more different patterns; a detector for capturing an image of a reflected light pattern which is reflected from the tissue as a result of the projected light pattern; and one or more processors coupled to the detector, the one or more processors being configured to perform a transform on the image of the reflected light pattern and determine oxygenation of each of a plurality of layers of the tissue in response to the transform of the image.

In an aspect, a method of measuring oxygenation of tissue comprises projecting a pattern onto the tissue with two or more wavelengths of light. The pattern is projected onto the tissue. A transform of the pattern is generated, and oxygenation of the tissue is determined in response to the transform of the projected pattern. While the projected pattern can be projected in many ways, in many instances the projected pattern comprises a one-dimensional pattern such as a one-dimensional sine wave. The projected pattern may comprise two superimposed sine waves in order to determine oxygenation of each of a plurality of layers of the tissue, such as a plurality of layers of retinal tissue. Alternatively, the projected pattern may comprise a two-dimensional pattern such as a two-dimensional sine wave.

The apparatus may comprise an ellipsometer to determine oxygenation of the retina at each of a plurality of layers of the retina. The projected pattern may comprise a plurality of superimposed patterns having different spatial frequencies, for example a first pattern having first spatial frequencies and a second pattern having second spatial frequencies. The first pattern may comprise a first wavelength of light and the second pattern may comprise a second wavelength of light. Each of the plurality of layers of the tissue can be mapped in response to the single frame. A splitter can be used to separate the first wavelength of light from the second wavelength of light imaged onto the detector comprising pixels in order to provide the measurement from a single frame from the detector.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
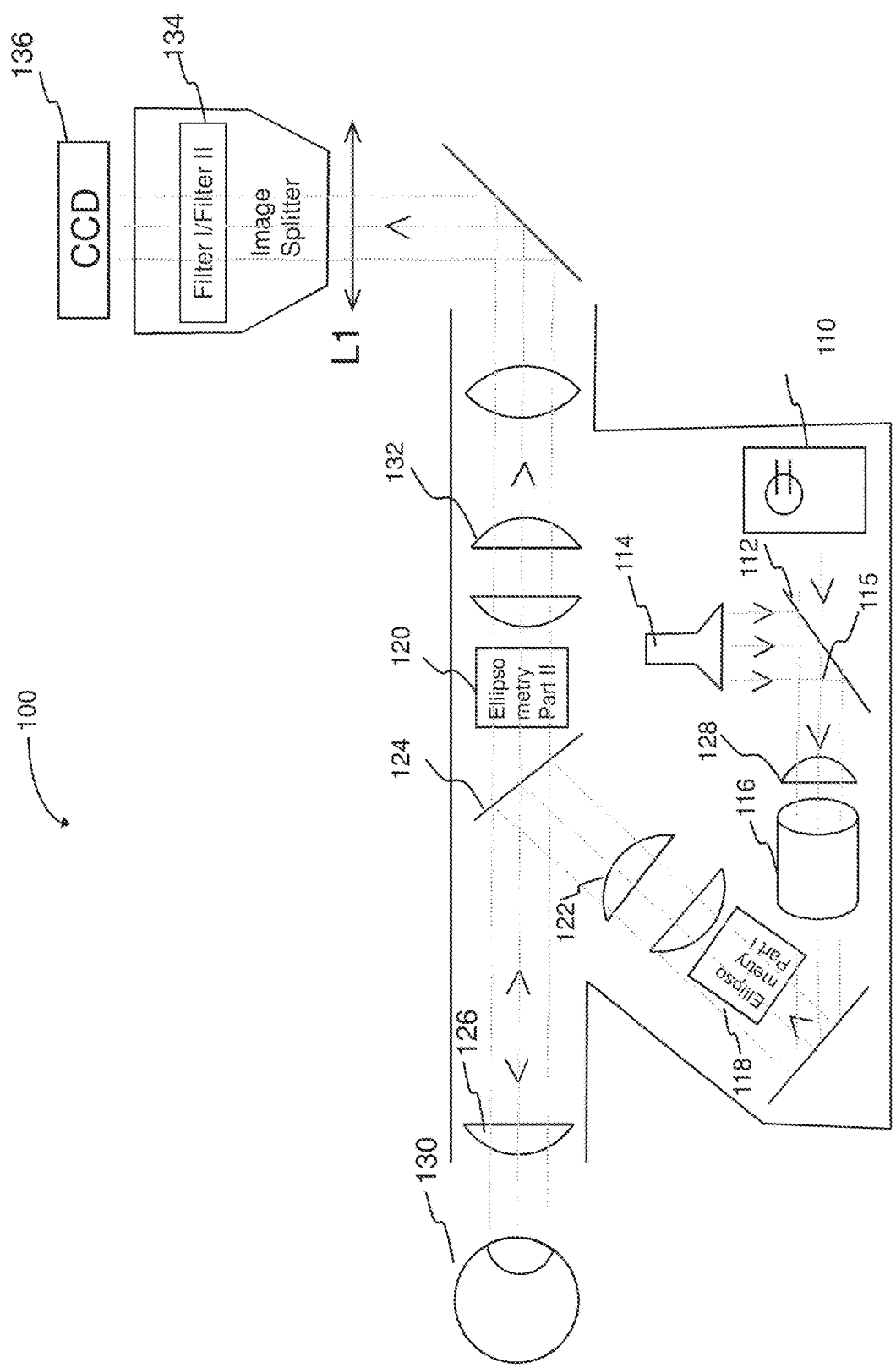
FIG. 1 illustrates a system for measuring oxygenation of retinal vasculature, in accordance with embodiments.

The methods and apparatus disclosed herein are well suited for measurements of many tissues, and can be configured in many ways. The methods and apparatus disclosed herein can be combined with prior methods and apparatus to provide improved measurement of tissue oxygenation, such ellipsometry as known to one of ordinary skill in the art.

Polarimetry is the measurement of the polarization of transverse waves, such as radio or light waves. Polarimetry is performed on electromagnetic waves that have traveled through or have been reflected, refracted, or diffracted by an object in order to characterize the object. Polarimetry of thin materials and surfaces is also known as ellipsometry. The measured signal is the change in polarization as the incident radiation (such as light waves) interacts with the material structure of interest (reflected, absorbed, scattered, or transmitted). The polarization change is quantified by the amplitude ratio and the phase difference. Because the signal depends on the thickness as well as the material properties, ellipsometry can be a useful tool for contact free determination of thickness and optical parameters of the material of interest. Upon the analysis of the change of polarization of light, ellipsometry can yield information about the material of interest. Ellipsometry can probe the complex refractive index or dielectric function tensor, which gives access to fundamental physical parameters. In this disclosure, ellipsometer can be used in calculating tissue oxygenation. In some embodiments, the ellipsometer can comprise a first portion and a second portion. The first portion of the ellipsometer can apply polarization to a light beam. The first portion of the ellipsometer can apply different polarizations to different components of a light beam, each component corresponding to a different spatial frequency. The second portion of the ellipsometer can enable a detection of a differential signal based on the different polarizations. Alternatively, a rotating polarizer can be used to polarize the light beam to be directed to the tissue. Information on different layers of the tissue can be distinguished by the changes in polarization angle of the reflected light beam over the incident light beam of the tissue Biological tissues are composed of a variety of chromophores, which are molecules that absorb light of characteristic wavelengths. If the amount of light that a tissue absorbs can be measured, then concentrations of the chromophores in the tissue can be calculated. This can be useful in clinical applications because some of chromophores in body tissue are markers of important clinical parameters, such as oxygenation. The attenuation of light in tissue is a function of both its absorption and scattering properties. Spatial frequency domain imaging (SFDI) can be used to separate the effects of scattering and absorption, and consequently, to quantify a set of chromophores. SFDI works by shining different patterns light on the tissue, capturing images of the remitted light, and processing the captured images. In this disclosure, SFDI is used in calculating tissue oxygenation. However, in conventional SFDI approach, a sinusoidal light pattern at different phases (0, $2\pi/3$, $4\pi/3$) is projected and three sample images are acquired. A reference with known optical properties is used to extract the AC/DC components of the reflectance. From these components, a steady-state diffusion equation can calculate the absorption and reduced scattering. Requiring three snapshots is problematic if the tissue has motion artifacts, such as with retinal imaging.

The present disclosure provides an improved optical method and apparatus for non-invasive measurement of tissue oxygenation. The method and apparatus disclosed herein are capable of measuring tissue oxygenation with a single snapshot of the tissue, thus can be advantageous in measuring oxygenation of a moving tissue such as retinal tissue of the eye. The method and apparatus disclosed herein enables measurement of oxygenation at each of a plurality of tissue by combining Dimensional Spatial Frequency Domain Imaging (SFDI) algorithm with ellipsometry to benefit from the best of each in a unified technique.

FIG. 1 illustrates a system 100 for measuring oxygenation of tissue. In some embodiments, the tissue can be retinal vasculature of an eye. A main light source 110 can be provided to illuminate a patient's tissue. The main light source can be an optical source emitting visible light and/or infrared light. In some instances, the main light source can be a laser source, such as a laser diode. In some embodiments, the main light source can be an infrared laser diode such as a near-infrared (NIR) diode. Alternatively, the main light source can be a LED.

In some embodiments, a secondary illumination source 114 can be provided in addition to the main light source. The light beam from the secondary illumination source can be mixed with the light beam from the main light source. In some instances, a reflecting surface 112 can be provided to mix the light beam from the main light source and the light beam from the secondary illumination source. For instance, the reflecting surface can be a beam splitter, such as a polarizing beam splitter, to allow the light beam mixture. The secondary illumination source can provide additional lighting as can be needed to more completely illuminate the tissue. The resulting beam 115 from the reflecting surface can comprise a plurality of light wavelengths. The light wavelengths can be preferentially chosen to be distributed about an isosbestic point of oxygenated blood. In some embodiments, the light beam can comprise two wavelengths of light. For example, the resulting beam can comprise wavelengths of 780 nm and 710 nm. Alternatively, the light beam can comprise more than two wavelengths of light. The resulting beam can be polarized, and can comprise a plurality of polarization components.

In some embodiments, the main light source can comprise an array of light emitting diodes, arranged to generate a sinusoidal pattern of light. In some instances, the main light source can generate light beam comprising a plurality of sinusoidal spatial modulations. In some embodiments, the main light source can comprise a first array of LEDs with a first spatial modulation frequency and a first polarization, and the secondary illumination source can comprise a second array of LEDs with a second spatial modulation frequency and a second polarization. The light beam from the main light source and the light beam from the secondary illumination source can be combined by the reflecting surface (for example, a polarizing beam splitter) while maintaining their separate polarizations for use in ellipsometry.

A diffuser 128 can be positioned in the path of the resulting beam from the reflecting surface, to eliminate high-order components. The diffuser can also generate a smooth sinusoidal pattern of light. The smooth sinusoidal pattern can be generated for each wavelength of light in the resulting beam. In such cases, a first polarization optics 118 and a second polarization optics 120, which will be described hereinafter, can be omitted.

The light beam can then then directed through shaping optics 116, which are configured to shape an incident, which is in a substantially Gaussian beam profile, into a toroidal beam profile. Thereafter, the light beam can be directed into first polarization optics 118.

The first polarization optics 118 can comprise a first portion of an ellipsometer, such that a first polarization can be applied to the light beam. A second polarization optics 120 can be provided in a later stage of the beam path, such that changes in polarization can be measured using known methods of ellipsometry. The first polarization optics 118 can apply different polarizations to different components of a light beam, each component corresponding to a different spatial frequency. For example, if a spatial modulation of beam intensity comprises a first and second spatial frequency component, each with different spatial frequencies, then the first polarization optics can be configured to apply a different polarization shift to each component, thereby allowing a differential signal to be detected based on the different polarization shifts measured as the beam passes through the second polarization optics 120 with polarization-based attenuation.

In some embodiments, the polarized light beam, which is polarized by the first polarization optics 118, can then be sent through focusing optics 122, as needed, to shape the light beam to have an appropriately-sized toroidal beam profile. The light beam can be reflected off a beam splitter 124, which comprises a reflective surface with a hole through which light can pass. The toroidal beam profile can be aligned such that its center coincides with the hole, such that most of the incident light of the beam is reflected toward a target tissue 130. The target tissue can be retina, which is a non-diffuse multi-layered tissue.

The light reflected toward the target tissue can be focused by a focusing lens 126 to fall on the target tissue. In some instance, the target tissue can be retina, the incident light can be focused by the focusing lens to fall on the retina, strike the patient's retina and scatter off. A significant portion of the scattered light can be reflected back toward the beam splitter 124, and can be directed through the hole in the beam splitter 124. Depending on the propagation depth into the tissue, the polarization angle of the reflected light beam can be rotated. As a result, the reflected light can have a slightly rotated polarization with respect to the polarization of the light beam incident on the tissue. This change in the polarization can be captured by the second polarization optics 120 and can be manifested as a reduction in the intensity of the captured light. Information on different layers of the tissue can be distinguished by the changes in polarization angle of the reflected light beam. In other words, the information of depth of tissue can be encoded in the angle of polarization of light.

Shaping optics 132 can then be provided in the light path to resize the light beam, and the light beam can be directed through a filter 134 to isolate the correct wavelengths of light. The filter can be an image splitter. For example, the filter can direct light of different wavelengths to different portions of a detector 136. The detector can be a CCD camera comprising an array of pixels. Each portion of the detector can measure an image of the corresponding wavelength. The light beam can strike the detector, allowing the light beam to be imaged. In some embodiments, the ellipsometer, which is comprises the first polarization optics and the second first polarization optics, can provide sensitivity to shifts in polarization of the light beam as it reflects off the target tissue. These detected shifts in polarization, such as rotations in polarization, can be used to calculate depths of light penetration, from which the method and apparatus as disclosed in this disclosure can detect depth dependent properties of blood oxygenation in the tissue.

The detector can be coupled to a processor which can be used to determine blood oxygenation based on measured signals from detector. The processor can further be coupled to a display to show measured results, such as a blood oxygenation map, to the user.

In some instances, if oxygenation as a function of depth is not to be determined, the ellipsometer can be omitted by removing the first polarization optics 118 and the second polarization optics 120.

Figure 2:
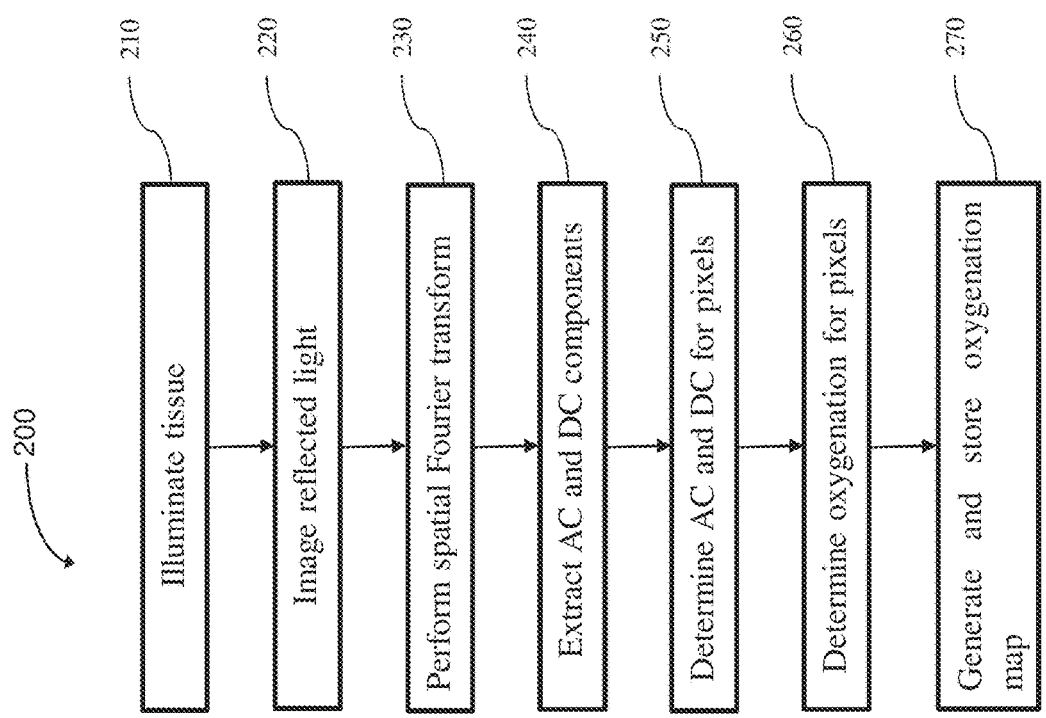
FIG. 2 illustrates a method of measuring blood oxygenation in a retina, in accordance with embodiments.

FIG. 2 illustrates a method 200 of measuring blood oxygenation in a tissue. In process or step 210, a tissue such as retina of the patient can be illuminated with illuminating light. The illuminating light can come from a main light source. The main light source can be an optical source emitting visible light and/or infrared light. In some instances, the main light source can be a laser source, such as an infrared laser diode. In some embodiments, the main light source can comprise an array of light emitting diodes, arranged to generate a sinusoidal pattern of light. The illuminating light can comprise a plurality of wavelengths, and be polarized to provide for ellipsometric imaging. In some embodiments, the illuminating light can comprise two wavelengths of light. Alternatively, the illuminating light can comprise more than two wavelengths of light. The illuminating light can comprise a sinusoidal intensity distribution; for example, a 1D sinusoid or a 2D sinusoid. In some cases, the illuminating light can comprise a plurality of summed sinusoids, including sinusoids summed with different weighting factors. The illumination can comprise a single imaging pulse, with a single sinusoidal intensity distribution. In some embodiments, the imaging pulse can comprise a plurality of frequencies and a plurality of sinusoidal spatial modulations, with each spatial modulation corresponding to a particular polarization.

The illuminating light can be allowed to reflect from the tissue for collection in an apparatus configured to measure light intensity. In some instances, the apparatus can be configured to determine light intensity as a function of polarization. For example, the light intensity can be determined as a function of polarization by using an ellipsometer.

In process or step 220, the reflected light from the tissue can be imaged by a detector. The detector can be an array of pixels, for example pixels of a CCD array. The signal of each pixel can correspond to an intensity as a function of polarization angle. This variation of intensity with respect to polarization angle can correspond to a variation of polarization angle with respect to penetration depth of light reflecting from the tissue. For instance, an increasing penetration depth can correspond to an increasing shift in polarization. By using an ellipsometer to detect the polarization shifts, the measurement in process or step 220 can be divided into a plurality of intensities as a function of depth, with each intensity corresponding to a different layer of depth in the tissue. This correlation between depth and polarization can be determined by using known properties of tissue and blood. Based on these properties, a comparison of intensity as a function of polarization can be used to determine oxygenation as a function of depth. Each of a plurality of wavelengths can be measured on corresponding pixels of the detector. For example, different wavelengths can be separated by filter to illuminate corresponding portions of the CCD.

In process or step 230, a spatial Fourier transform can be performed. Based on this spatial Fourier transform, in process or step 240, a plurality of frequency components can be extracted, corresponding to AC and DC components. The AC and DC components can correspond to sinusoidal components, and each AC component can correspond to a particular polarization. In some instance, the AC component is the sinusoidal component where frequency is 0, and a DC component may be the sinusoidal component where frequency is an imposed spatial frequency f. The intensities of each of the DC and AC components can be determined, and a frequency-specific intensity can be determined for each. For example, a general form of AC and DC components can correspond to the intensity equation I=A+B cos(kx), in which A is the DC component and B is the AC component.

In process or step 250, AC and DC components can be determined for a plurality of pixels of the detector (for example, the CCD). Specific Fourier components corresponding to each of the AC and DC intensities can be isolated with only a modest decrease in spatial resolution. For example, AC and DC intensities can be determined with a resolution loss factor of 10 to 1. Thus, for example, a 1000×1000 detector can produce an image for each component with an effective resolution of about 100×100.

In process or step 260, blood oxygenation levels can be determined for a plurality of pixels. The blood oxygenation level of each pixel can be determined by a comparison of the intensities of the AC and DC components of reflected light for the plurality of wavelengths, from which absorption can be determined, using a modified Beer-Lambert absorption model. Known absorption properties of tissue, and especially of oxygenated and deoxygenated blood, can be used to calculate absorption based on the relative intensities of the AC and DC components. The blood oxygenation levels can further be determined as a function of depth, where different polarizations of light corresponding to different depths. This determination can be represented, for example, as a map of blood oxygenation. Measurement sensitivity of 3.5% or better can be achieved. Thus, it can be possible to diagnose small changes in blood oxygenation, where increased oxygenation of about 3% to 5% can be a warning sign of diseases such as diabetic retinopathy. Because this determination can be made from a single image, noise sources such as tissue movement between images can be avoided.

In process or step 270, a blood oxygenation map can be generated and stored to a computer-readable medium. The blood oxygenation map can be further displayed to a user. If the blood oxygenation map indicates an increased oxygenation above a threshold, a warning can be provided, indicating that the user can be in danger of diseases such as diabetic retinopathy. The threshold can be a predefined threshold, or can be based on a comparison to prior measurements of blood oxygenation.

Although the above processes and steps show a method of measuring tissue oxygenation in accordance with some embodiments, a person of ordinary skill in the art will recognize many variations based on the teachings described herein. The processes and steps can be completed in a different order. Processes and steps can be added or deleted. Some of the processes and steps can comprise sub-processes and sub-steps of other processes and steps. Many of the processes and steps can be repeated as often as desired by the user.

In some embodiments, multiple spatial frequencies can be used and each frequency's polarization change can be calculated to average out an error caused by scattering in detecting the polarization angle, although retinal layers are more absorptive. In some instances, green and red wavelengths can be used to increase a contrast if the light beam generated by the main light source (e.g., NIR) does not provide enough contrast. In some instances, if there is insufficient contrast, the output can be limited to the average $SO_2$ in each section of the ETDRS map.

Figure 3B:
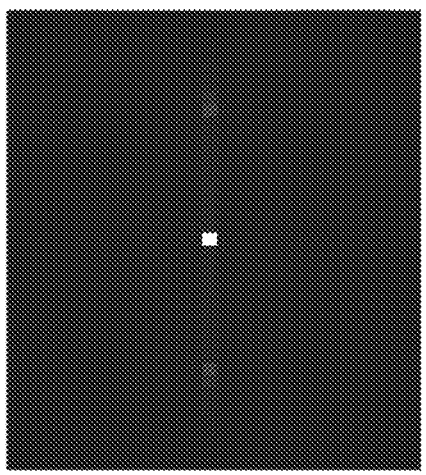
FIG. 3B illustrates a Fourier transform of a sinusoidal pattern, in which AC and DC components correspond to different Fourier peaks, in accordance with embodiments.
Figure 3A:
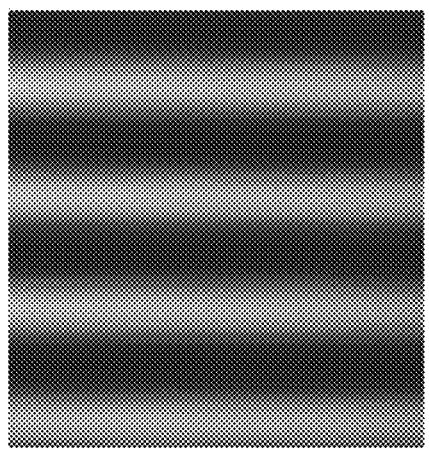
FIG. 3A illustrates a sinusoidal pattern, which can be applied to light emitted from LEDs to impart a spatial frequency in a light beam, in accordance with embodiments.

FIG. 3A illustrates a sinusoidal pattern, which can be applied to light emitted from the main light source to impart a spatial frequency in a light beam, as disclosed herein. FIG. 3B illustrates a Fourier transform of a sinusoidal pattern, in which AC and DC components correspond to different Fourier peaks. The central peak corresponds to the DC component, and the side peaks correspond to AC components. Each component can individually be extracted to generate a corresponding two-dimensional intensity distribution. For example, unwanted peaks can be masked off and an inverse Fourier transform can be applied to generate a two-dimensional image corresponding only to unmasked spatial frequencies.

Figure 4:
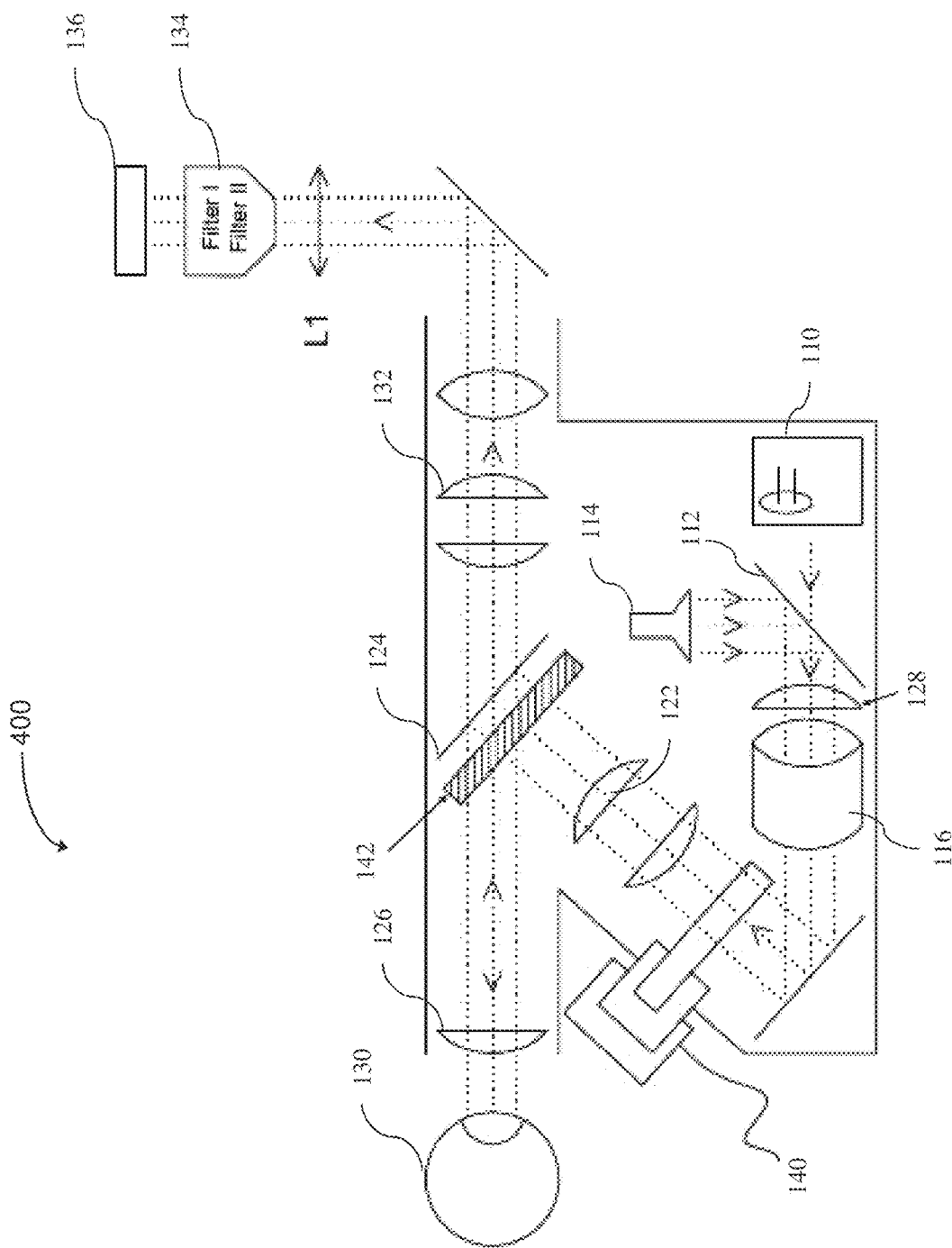
FIG. 4 illustrates a system for measuring oxygenation of retinal vasculature, in accordance with embodiments.

FIG. 4 illustrates a system 400 for measuring oxygenation of retinal vasculature, in accordance with embodiments. In some embodiments, the tissue can be retinal vasculature of an eye. The main light source 100 can be a laser source, such as a laser diode or an infrared laser diode such as a near-infrared (NIR) diode. In some embodiments, the main light source can be a LED. A secondary illumination source 114 can be provided in addition to the main light source. The light beam from the secondary illumination source can be mixed with the light beam from the main light source at a reflecting surface 112. In some instances, the reflecting surface can be a beam splitter, such as a polarizing beam splitter, to allow the light beam mixture. The resulting beam 115 from the reflecting surface can comprise a plurality of light wavelengths. The light wavelengths can be preferentially chosen to be distributed about an isosbestic point of oxygenated blood. In some embodiments, the illuminating light can comprise two wavelengths of light. For example, the resulting beam can comprise wavelengths of 780 nm and 710 nm. Alternatively, the illuminating light can comprise more than two wavelengths of light.

The resulting beam 115 can then pass through a diffuser 128 to eliminate high-order components. The light beam can then then directed through shaping optics 116, which are configured to shape an incident light, which is in a substantially Gaussian beam profile, into a toroidal beam profile. Thereafter, the light beam can be directed into a modulation stage 140.

At the modulation stage 140, the light beam can be patterned by passing through a structure attached to a motorized stage. The motorized stage can be shifted to create different phases and frequencies. In some embodiments, the uniform light beam from the main light source can be patterned into a sinusoidal pattern of different phases and frequencies at the modulation stage 140. The light beam can then then directed through focusing optics 122, as needed, to shape the light beam to have an appropriately-sized toroidal beam profile.

The light beam can then be directed to a rotating polarizer 142 which polarizes the light beam to be impinged on the tissue. In some instances, the rotating polarizer can be driven by a motor. The polarized light beam can then be reflected off a beam splitter 124, which comprises a reflective surface with a hole through which light can pass. The light beam can be reflected at the beam splitter toward the target tissue 130. The target tissue can be retina. The light reflected toward the target tissue can be focused by a focusing lens 126 to fall on the target tissue. In some instance, the target tissue can be retina, the incident light can be focused by the focusing lens to fall on the retina, strike the patient's retina and scatter off. A significant portion of the scattered light can be reflected back toward the beam splitter 124, and can be directed through the hole in the beam splitter 124.

Depending on the propagation depth into the tissue, the polarization angle of reflected light beam can be rotated. As a result, the reflected light can have a slightly rotated polarization with respect to the polarization of the light beam incident on the tissue. This change in the polarization can be captured by the polarizer and can be manifested as a reduction in the intensity of the captured light. Information on different layers of the tissue can be distinguished by the changes in polarization angle of the reflected light beam. In other words, the information of depth of tissue can be encoded in the angle of polarization of light.

Shaping optics 132 can then be provided in the light path to resize the light beam, and the light beam can be directed through a filter 134 to isolate the correct wavelengths of light. The filter can be an image splitter. For example, the filter can direct light of different wavelengths to different portions of a detector 136. The detector can be a CCD camera comprising an array of pixels. Each portion of the detector can measure an image of the corresponding wavelength.

In the method and apparatus as disclosed in present disclosure, the incident polarized light is spatially modulated and the reflectance and polarization change through different retinal layers are measured. The information from absorption is encoded in the change of reflectance for different spatial frequencies. The optical information from different layers is encoded in the shift of polarization angle. In contrary to conventional ellipsometry where one would need to scan a range of incidence angles to reconstruct the polarization angle changes, with the method and apparatus as disclosed in present disclosure, each spatial frequency corresponds to a unique incidence angle. Thus, in one snapshot, all the information needed to map the multilayer retinal structure can be captured. In some instances, the one snapshot can be selected from a plurality of snapshots of the tissue. For example, a 1-second video can be captured on the tissue which contains 60 frames, and one snapshot having the optimal imaging quality can be selected. The selection of snapshot can be performed manually or automatically by algorithms. In some embodiments, more than one snapshot can be needed if more than two wavelengths of light are used to calculate the oxygenation of tissue such as retina. For example, different spatially modulated light can illuminate in different snapshots.

The method and apparatus as disclosed in present disclosure are based on the physics of retinal layers. No assumptions or a priori knowledge about the structure is needed. The index of reflectance, absorption coefficient, and scattering coefficient can be calculated from Equation 1:

$$n_t = n_i \sin(\theta_i) \left\{ 1 + \tan(\theta_i)^2 \left( \frac{1 - \tan(\psi)e^{i\Delta}}{1 + \tan(\psi)e^{i\Delta}} \right)^2 \right\}^{\frac{1}{2}}$$

where: n is the index of refraction, $\theta$ is an angle of radiation, $\psi$ is ellipsometry angle, $\Delta$ is ellipsometry phase, i is incident medium and t is transmitted radiation. In each snapshot, at least two spatial frequencies can be used to calculate the unknown parameters (e.g., absorption and scattering coefficients).

With the method and apparatus as disclosed in present disclosure, the absorption of Layer 2 with ≥95% accuracy can be accurately detected in vivo in a patient and similar accuracy can be obtained in a model. The oxygenation throughout the retinal layers can be measured non-invasively with ~4% sensitivity (e.g., being sensitive to 4% changes in $SO_2$), which is powerful enough to detect the onset of DR prior to structural damage in vivo in patients. Therefore, the method and apparatus as disclosed in present disclosure can be capable of detecting a change in oxyhemoglobin ≤0.3 g/dL and achieving ≤2% error in hemoglobin compared with spectroscopy.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A method of measuring oxygenation of a tissue, the method comprising:
   projecting a light pattern onto the tissue;
   capturing a first image of a reflected light pattern which is reflected from the tissue;
   performing a transform on the reflected light pattern; and
   determining an oxygenation of the tissue in response to the transform of the reflected light pattern.

2. The method of claim 1, wherein the performing the transform comprises performing a spatial Fourier transform.

3. The method of claim 2, wherein the performing the transform further comprises determining the oxygenation in response to frequency components of the spatial Fourier transform of the reflected light pattern.

4. The method of claim 1, wherein the determining the oxygenation of the tissue comprises determining an oxygenation of each of a plurality of layers of the tissue in response to the transform.

5. The method of claim 1, further comprising generating an oxygenation map of the tissue in response to the transform of the reflected light pattern.

6. The method of claim 1, wherein the tissue comprises retinal tissue of an eye.

7. The method of claim 1, wherein the light pattern comprises a one-dimensional pattern comprising a one-dimensional sine wave.

8. The method of claim 1, wherein the projecting the light pattern onto the tissue comprises projecting two or more wavelengths onto the tissue.

9. The method of claim 1, wherein the determining the oxygenation of the tissue comprises using less than three images of the reflected light pattern, wherein the less than three images comprises at least the first image.

10. The method of claim 1, wherein the capturing the first image of the reflected light pattern comprises using a detector comprising a plurality of pixels, and wherein the method further comprises determining an amount of light scattering and an amount of light reflection for each pixel of the plurality of pixels.

11. An apparatus to measure oxygenation of a tissue, the apparatus comprising:
    a light source configured to emit a light pattern to be projected onto the tissue;
    a detector for capturing a first image of a reflected light pattern which is reflected from the tissue; and
    one or more processors operatively coupled to the detector and to a non-transitory computer readable storage medium comprising instructions which, when executed by the one or more processors, are configured to: perform a transform on the first image of the reflected light pattern and determine an oxygenation of the tissue in response to at least the transform of the first image of the reflected light pattern.

12. The apparatus of claim 11, wherein the transform is a spatial Fourier transform.

13. The apparatus of claim 12, wherein the instructions are configured to determine the oxygenation in response to frequency components of the spatial Fourier transform of the reflected light pattern.

14. The apparatus of claim 11, wherein the instructions are configured to determine an oxygenation of each of a plurality of layers of the tissue in response to the transform.

15. The apparatus of claim 11, wherein the instructions are configured to generate an oxygenation map of the tissue in response to the transform of the reflected light pattern.

16. The apparatus of claim 11, wherein the detector comprises a plurality of pixels, and wherein the instructions are configured to determine an amount of light scattering and an amount of light reflection for each pixel of the plurality of pixels.

17. The apparatus of claim 11, wherein the tissue comprises retinal tissue of an eye.

18. The apparatus of claim 11, wherein the light pattern comprises a one-dimensional pattern comprising a one-dimensional sine wave.

19. The apparatus of claim 11, wherein the light pattern comprises two or more wavelengths.

20. The apparatus of claim 11, wherein the instructions are configured to determine the oxygenation of the tissue using less than three images of the reflected light pattern, wherein the less than three images comprises at least the first image.

* * * * *